United States Patent [19]

Higuchi et al.

[11] 3,995,631
[45] Dec. 7, 1976

[54] OSMOTIC DISPENSER WITH MEANS FOR DISPENSING ACTIVE AGENT RESPONSIVE TO OSMOTIC GRADIENT

[75] Inventors: Takeru Higuchi, Lawrence, Kans.; Harold M. Leeper, Mountain View, Calif.

[73] Assignee: Alza Corporation, Palo Alto, Calif.

[22] Filed: Sept. 25, 1972

[21] Appl. No.: 291,686

Related U.S. Application Data

[63] Continuation-in-part of Ser. No. 106,161, Jan. 13, 1971, abandoned.

[30] Foreign Application Priority Data

Jan. 11, 1972 Israel .................................. 38539

[52] U.S. Cl. .................................. 128/260; 222/95; 128/270; 128/271
[51] Int. Cl.² .................. A61M 31/00; B65D 35/28
[58] Field of Search ............. 210/23; 128/127–131, 128/172, 213, 252, 260, 261, 271, 272; 222/193, 130, 94, 95, 97, 105, 106, 386, 386.5, 389

[56] References Cited
UNITED STATES PATENTS

| | | | |
|---|---|---|---|
| 2,962,023 | 11/1960 | Chappaz et al. .............. | 128/271 X |
| 3,468,308 | 9/1969 | Bierman ........................ | 128/216 |
| 3,496,937 | 2/1970 | Balson .......................... | 128/216 |
| 3,556,992 | 1/1971 | Massucco ...................... | 210/23 |
| 3,561,644 | 2/1971 | Works ........................... | 222/95 |
| 3,604,417 | 9/1971 | Stolzenberg ................... | 128/213 |
| 3,641,237 | 2/1972 | Gould et al. .................. | 128/260 X |
| 3,732,865 | 5/1973 | Higuchi et al. ................ | 128/260 |
| 3,760,984 | 9/1973 | Theeuwes ...................... | 128/260 X |

OTHER PUBLICATIONS

Govindan and Sourirajan, "Reverse Osmosis ... Membranes", I & EC Process Design and Development; vol. 5, No. 4, pp. 422–429, 10–1966.

*Primary Examiner*—Aldrich F. Medbery
*Attorney, Agent, or Firm*—Thomas E. Ciotti; Paul L. Sabatine; Edward L. Mandell

[57] ABSTRACT

An osmotic active agent dispenser is comprised of a chamber having controlled permeability to an external fluid, i.e., water, and containing an osmotically effective solute which, in solution, exhibits an osmotic pressure gradient against said external fluid, said chamber housing a flexible bag of relatively impervious material containing an active agent and provided with means or dispensing head for releasing said active agent to the exterior of the dispenser. The flexible bag is disposed within the said housing chamber such that as the, e.g., water permeates from the external environment through the permeable walls of the chamber and migrates or diffuses by osmosis into the solution contained therein, same increases in volume thereby generating mechanical compressing or deflating force on the flexible bag, which force in turn ejects the active agent out of the apparatus at an osmotically controlled rate over a prolonged period of time.

10 Claims, 8 Drawing Figures

OSMOTIC DISPENSER WITH MEANS FOR DISPENSING ACTIVE AGENT RESPONSIVE TO OSMOTIC GRADIENT

CROSS REFERENCE TO RELATED APPLICATIONS

This application is a continuation-in-part of our abandoned application, Ser. No. 106,161, filed Jan. 13, 1971, assigned to the assignee of the present application.

Other related applications comprise:

Takeru Higuchi copending application, Ser. No. 106,131, filed Jan. 13, 1971, and now U.S. Pat. No. 3,760,805, also assigned to the assignee of the present application;

Takeru Higuchi and Harold M. Leeper copending application, Ser. No. 106,130, filed Jan. 13, 1971, and now U.S. Pat. No. 3,732,865, also assigned to the assignee of the present application;

Harold M. Leeper copending application, Ser. No. 106,132, filed Jan. 13, 1971, and now U.S. Pat. No. 3,760,806 also assigned to the assignee of the present application;

Takeru Higuchi and Harold M. Leeper copending application, Ser. No. 106,031, filed Jan. 13, 1971, and now U.S. Pat. No. 3,760,804, also assigned to the assignee of the present application;

Masahiro Nakano, Takeru Higuchi and Anwar Hussain copending application, Ser. No. 106,133, filed Jan. 13, 1971, now abandoned, also assigned to the assignee of the present application;

Takeru Higuchi and Harold M. Leeper abandoned application, Ser. No. 127,253, filed Mar. 23, 1971, also assigned to the assignee of the present application; and Takeru Higuchi copending application, Ser. No. 127,252, filed Mar. 13, 1971, now abandoned, also assigned to the assignee of the present application.

FIELD OF THE INVENTION

This invention relates to an osmotic dispenser, and, more especially, to an osmotic dispenser, simple in construction, capable of releasing to its outside environment concentrations of active agent at an osmotically controlled rate over a continuous and prolonged period of time.

DEFINITION OF TERMS

The expression "active agent" as used herein denotes any drug (as defined, infra); composition in any way affecting any biological entity; substance having a nutrient or stimulating action, or growth inhibiting, destroying or any regulating action on plant growth, controlled or otherwise; substance to be assimilated by any organism, e.g., human being, animal, or lower order organism, for its nourishment or for regulating its growth; substance exhibiting any of the above activities to be directly applied to the habitat, surroundings or environment of any of the above organisms; and substance having any other effect on any other environment, especially any aqueous environment.

Therefore, suitable active agents for use with the dispenser of this invention include, without limitation, those which are generally capable of:

1. Preventing, alleviating, treating or curing abnormal or pathological conditions of the living body by such means as destroying a parasitic organism or limiting the effect of the disease of abnormality by chemically altering the physiology of the host or parasite;

2. Maintaining, increasing, decreasing, limiting or destroying a physiologic body or plant function, e.g., vitamin compositions, sex sterilants, fertility inhibitors, fertility promotors, growth promoters, and the like;

3. Diagnosing a physiological condition or state;

4. Controlling or protecting an environment or living body by attracting, disabling, inhibiting, killing, modifying, repelling or retarding an animal or microorganism, such as food and non-food baits, attractants and lures, biocides, pesticides, algicides, parasiticides, rodenticides, insecticides, fungicides, and the like;

5. Preserving, disinfecting or sterilizing; and

6. Controlling or affecting generically an environment, as by introducing a catalyst or metering a reactant into a reacting chemical system, or by effecting any chemical process therein, such as a fermentation, including propagation and/or attenuation of a microorganism.

The terms "environment", "surroundings" and "habitat" as used hereinabove and herein denote any prospective situs for the osmotic dispenser of this invention, or at least for the external fluid permeable membrane component thereof, which is comprised of or will provide sufficient fluid, e.g., water, for absorption into the device to develop the needed osmotic pressure on which its motive force depends; and implicit in the foregoing definition of "active agent" — one that will develop its action in the presence of such environment, surroundings or habitat, or one that will develop its action on a remote and/or another environment, which need not be fluid or aqueous, as hereinafter described and illustrated.

BACKGROUND OF THE INVENTION

Many and varied compositions, products, appliances, depositors, applicators, dispensers, injectors and devices are well known in the art in which the timing or spacing of administration or absorption of an active agent is regulated by the structure or physical arrangement of elements so that a single administration provides a gradual but continuous or sustained feeding of the active agent to a system by slow or differential release. All of such prior art devices and the like, however, are characterized by at least one feature which adversely affects control over their rate of sustained or differential release or which detracts from the practical benefits attendant the long-term continuous administration of various active agents both to humans, animals, and into other environments.

An osmotic dispenser too has been proposed which is capable of delivering drug solution at a relatively constant rate. See Rose and Nelson, *Austral. J. Exp. Biol.*, 33 pp. 415 – 420 (1955). The Rose et al injector consists of three compartments and a clamp to hold a semipermeable membrane. The motive force of the injector depends on the osmotic pressure developed by a saturated aqueous solution of Congo red against water. This solution is contained in a partially collapsed rubber compartment and is separated from a second water compartment by the semi-permeable cellophane membrane. The partially collapsed bag is placed in a glass ampoule, with the drug compartment of the device being defined by the space between the Congo red bag and the glass ampoule. The ampoule is also provided with drug release means and when the drug compartment is charged with a drug solution by osmosis water will move into the Congo red solution thus expanding the rubber compartment and providing the mechanical force to eject the drug out of the apparatus.

The Rose et al device, however, has substantial inherent disadvantages which has prevented its wide acceptance by the medical community. In the first place, the use of a solution as the drug vehicle (1) will not permit high concentration of drug to be embodied within the device; (2) such solutions exhibit the deleterious tendency to be released from the device by simple leaching; and (3) many chemical substances on prolonged storage in a dissolved state undergo chemical deterioration. The reference injector is moreover cumbersome in that it depends for its motive force on a separate water compartment rather than its environment. In addition, the Rose et al device is essentially only a research or experimentation tool, is complex in construction, and is at least literally restricted to a Congo red solution to produce the osmotic driving force and to a cellophane osmotic membrane. See also Rose and Nelson, *Austral. J. Exp. Biol.*, 33 pp. 411 – 414 (1955).

SUMMARY OF THE INVENTION

Accordingly, it is a primary object of this invention to provide an osmotic dispenser, simple in construction, which exhibits all of the various active agents both to animals, humans, and into other environments.

Another object of this invention is to provide an improved osmotic dispenser which overcomes problems inherent in related devices heretofore proposed.

Another object of this invention is to provide an improved osmotic dispenser which will permit high concentrations of active agent to be embodied therein, and which high concentrations of active agent will not exhibit the tendency to be leached from the device nor be decreased in potency by chemical breakdown.

Another object of this invention is to provide an osmotic active agent dispenser which depends for its motive force on its environment.

Still another object of this invention is to provide an osmotic dispenser, the osmotic membrane of which can be fabricated from many and varied suitable materials, and which is capable of using a variety of solutions of osmotically effective solutes to produce the osmotic driving force.

Yet another object of this invention is to provide an osmotic dispenser of simple design which will release active agent solution, or gel, or semisolid active agent formulation, at a controlled rate over a prolonged period of time.

In attaining the objects of this invention, one feature resides in an osmotic dispenser comprised of a rigid housing member or chamber having controlled permeability to an external fluid, e.g., water, and containing an osmotically effective solute which, in solution, exhibits an osmotic pressure gradient against said fluid. Disposed within and occupying a portion of the volume of the said rigid housing member is a flexible bag of relatively impervious material containing the active agent, advantageously a drug, preferably in a gel, paste or other semisolid state (albeit a solution or concentrated solution of active agent will sometimes suffice). The said flexible bag is disposed within the said rigid housing member of controlled permeability to external fluid such that as the fluid diffuses from the environment by osmosis into the solution contained in the said housing member, the said solution increases in volume, thus exerting mechanical force on the active agent containing flexible bag, which mechanical force in turn ejects the active agent out of the apparatus. For purposes of permitting the active agent to be squeezed out of the said flexible bag, same is provided with any suitable active agent release means or dispensing head to the exterior of the device, e.g., long plastic tubing extending through the housing member, or duct like fine tubule connections or capillary ducts therethrough.

Other objects, features and advantages of this invention will become more apparent from the following description when taken in conjunction with the accompanying drawings and wherein like reference numerals are used to indicate like or equivalent parts.

DETAILED DESCRIPTION OF THE INVENTION

Figure 1:
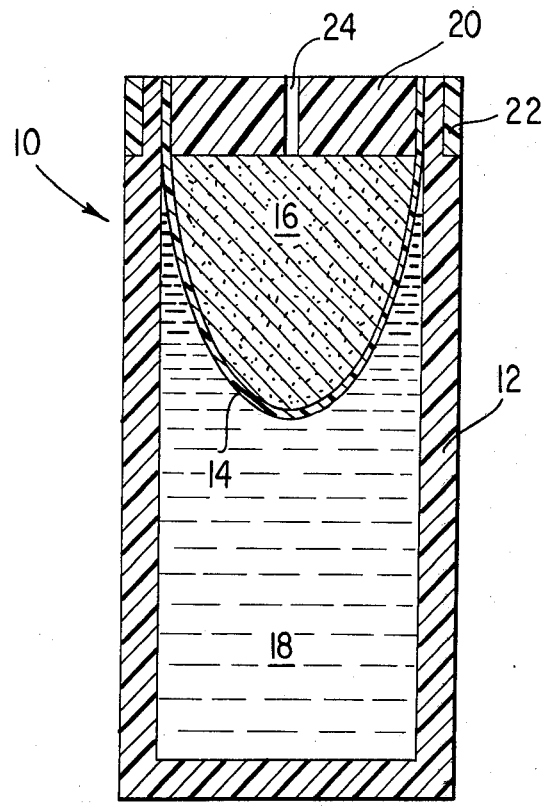
FIG. 1 is a cross-sectional view of an osmotic dispenser of this invention.
Figure 1A:
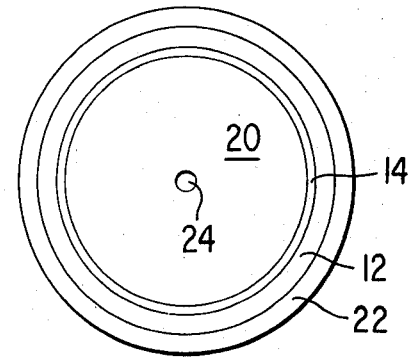
FIG. 1a is a top view of the osmotic dispenser of FIG. 1.

In one embodiment in accordance with this invention, as illustrated in FIG. 1, an osmotic dispenser 10 is comprised of a rigid canister 12, at least a portion of the wall membrane defining the same exhibiting controlled permeability to an external fluid, e.g., water, as hereinafter more fully explained. Housed within the canister 12 is a flexible bag 14 of relatively impervious material. The said flexible bag 14 contains an active agent formulation 16, advantageously a drug, preferably in a gel, paste or other semi-solid state (albeit a solution or concentrated solution of active agent will sometimes suffice), and the active agent, if a drug, is preferably normally carried in an oil phase, such as cocoa butter. The volume of the canister 12, other than that occupied by the flexible bag 14 and its active agent content 16, is occupied by a solution 18 of an osmotically effective solute which exhibits an osmotic pressure gradient against said external fluid. The open end of canister 12 is tightly sealed or closed off with rigid, impervious dispensing head, plug or delivery cap 20, with the open end of the flexible bag 14 being concentrically secured therebetween (see also FIG. 1a). In this manner a tight barrier is maintained between and among the active agent phase 16 in the flexible bag 14, the osmotic fluid 18 in the canister 12, and the external environment of the device 10. Without this tight barrier, undesirable contamination could take place. The dispensing head 20 is preferably snapped or press-fit in place with the flexible bag 14 either being already circumferentially tightly secured thereto or to the upper, inner periphery of the canister 12. Alternatively, these three elements may conveniently be heat sealed together, and, as an aid in maintaining the tight barrier, a chamfered polycarbonate retaining ring 22 may optionally be press-fit about the top of the device 10. Active agent release means 24 provides communication from the interior of the flexible bag 14 to the exterior of the device 10, in this instance the said means 24 being a capillary duct or opening bored into the dispensing head 20, said duct advantageously being approximately 0.0625 inch in diameter.

To use the osmotic active agent dispenser of FIG. 1, the device, when the active agent is a drug or other agent for treating, etc., a living organism, is either physically inserted or surgically implanted in the body of the organism, typically a mammal, or is administered via the gastrointestinal tract. Once in place, water or other external fluid will be absorbed therein from either body tissues or body fluids through the area of the canister 12 which exhibits the controlled permeability to water and in an effort to reach osmotic equilibrium, i.e., a transition from hypertonicity to isotonicity. As the fluid flows by osmosis into the canister 12 the volume of the solution 18 is thus increased and corresponding pressure is exerted against the confined flexible bag 14 containing the drug formulation 16. Such pressure serves to squeeze out the drug content 16 of the bag 14 through the conduit 24 at an osmotically controlled and constant rate into the external environment. There is accordingly provided the gradual and controlled constant release of drug or similar agent directly to the body or affected organ thereof over a prolonged period of time. Moreover, the use of any semisolid drug vehicle will reduce the tendency to release the drug, or any other active agent for that matter, by leaching and will permit high concentrations thereof to be embodied within the device.

The design of the canister 12 is such that given area of the wall members defining the same displays permeability to the external fluid at an osmotically controlled rate from the exterior surfaces to the interior compartment thereof. Said canister, therefore, is either of unit or composite construction and is advantageously comprised of semi-permeable membrane, with same either defining an integral wall member of the canister, or a lining, or in some manner is laminated thereto or otherwise disposed in the desired functional relationship.

Figure 2:
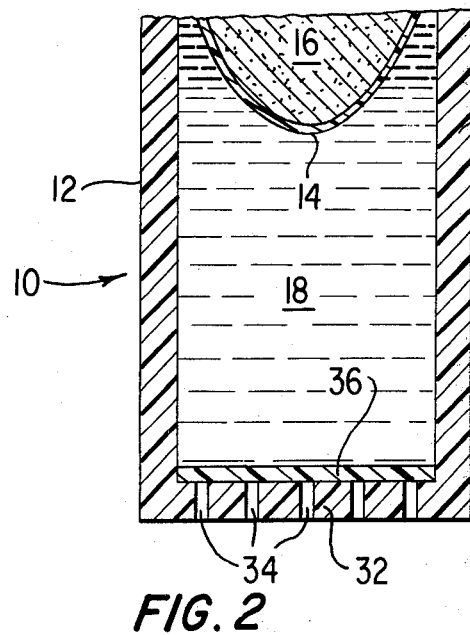
FIG. 2 is a cross-sectional view of another osmotic dispenser of this invention.

In FIG. 2, for example, there is illustrated an osmotic active agent dispenser 10 wherein the canister 12 is comprised of rigid, impervious, cylindrical plastic side wall member 30 and bottom wall member 32 integral therewith. Bored into the said bottom wall member 32 are a plurality of orifices or ducts 34, each preferably about 1/16 inch in diameter. It will thus be appreciated that, being highly porous, only the bottom wall member 32 of the canister 12 is capable of admitting water or other fluid into the device, the said cylindrical side wall member 30 remaining fluid impenetrable. It is not intended that the highly porous bottom wall member 32 in any way act as a barrier to or restrict the transport of fluid. Securely affixed and supported atop the said perforated bottom wall member 32 is a flat disc 36 of membrane which exhibits controlled permeability to external fluid, e.g., water. The membrane 36 may, for example, either be adhesively secured in place or may be lined or laminated to, or cast from solution atop the said bottom wall member 32. The aforementioned casting atop the porous wall 32 is advantageously perfected by depositing the film or disc from a solution of membrane forming material in a solvent, e.g., a 20% solution of cellulose acetate in an acetone-ethanol-ethyl lactate mixed solvent, 65% – 20% – 15%, respectively. In casting the film, care should be taken that the pores of the wall member 32 do not become clogged. And it is of course intended that the seal between the membrane 36 and the porous wall 32 be watertight such that fluid is permitted access to the interior of the device only by diffusing by osmosis through the said membrane 36. As too will be appreciated, it is also possible that the membrane 36 be affixed beneath the said bottom wall member 32. The design of the FIG. 2 is moreover unique in that it requires a membrane of but limited surface area relative to the overall dimensions of the canister. This because of the ready availability of the highly water-permeable cellulose acetate membranes designed for use in reverse osmosis processes for water desalination. These membranes, typically and preferably anisotropic membranes, are highly permeable to water (allow relatively rapid rates of water transmission) but are relatively impermeable to salt, thus permitting their use in relatively small exposure area devices. And water will migrate into the dispenser only at the point of exposure of the membrane 36 with the outside environment via the ducts 34.

Figure 3:
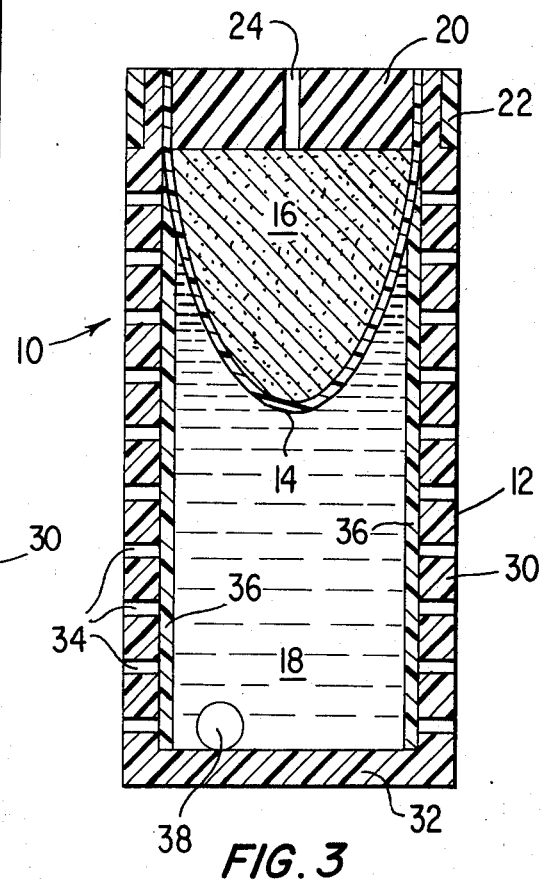
FIG. 3 is a cross-sectional view of yet another osmotic dispenser of this invention.

Optionally, in an alternative embodiment of the invention, a separator of porous paper, fabric or the like can conveniently be disposed between the bottom wall member 32 and the membrane 36. This prevents the membrane from being punctured or drawn into too tight a contact with the canister, thereby assuring that the entire membrane is exposed to the fluid environment. The immediately above option also applies to a device such as illustrated in FIG. 3. Furthermore, use of the porous separator aids in the aforesaid embodiment of casting the membrane from solution, same providing a ready-made molding or casting surface with no danger of orifices 34 clogging.

In FIG. 3 there is depicted an osmotic active agent dispenser 10 which allows for higher available exposure area of membrane 36 and, accordingly, which design takes advantage of the availability of a far greater number of membranes than the semi-permeable, anisotropic cellulose acetate membranes of the type used in reverse osmosis water desalination. In this embodiment it is the rigid, impervious, cylindrical plastic side wall member 30 which is provided with the plurality of orifices or ducts 34, again, each preferably being about 1/16 inch in diameter, and it is this perforated wall 30 which is tightly fitted, as in FIG. 2, with the membrane 36, in this instance a membrane of cylindrical configuration. Many and varied designs intermediate in construction between the designs of the FIG. 2 and FIG. 3 devices, insofar as available exposure area of membrane is concerned, are of course within the scope of the invention.

In some instances, the dispenser is of insufficient specific gravity to maintain placement at the desired location. For example, for use in the rumen of polygastric animals, the weight should be sufficient to provide a specific gravity of at least 1.5. In those instances of insufficient specific gravity, therefore, a weight or ballast can be placed in the device, such as the steel ball 38 of FIG. 3. Other suitable weights comprise iron plugs, iron ore tablets, brass plugs, ceramic plugs, or the like.

When the active agent is other than a drug or similar agent, or is intended for use other than in a living organism, the device is introduced into the desired fluid environment to produce the desired effect exactly as would be any of the known means for accomplishing a like result. And this is generally a mere physical insertion, such as by placing a pesticide containing device in a river or stream, or a catalyst containing device in an, e.g., aqueous reaction medium.

If desired, long flexible tubing of polythene or the like can be extended from the dispensing head of the device of either of FIGS. 1, 2 or 3. In such manner the device can be deposited at a site remote from the desired point of application and still release its active agent contents through the dispensing head and then through the tube directly to said point. This permits placement of the dispenser in a fluid environment and release of the active agent into another environment which need not be fluid. The dispensing head can also be provided with a check valve, for example, a one way bell valve, to prevent back flow of active agent or other materials from the external environment into the device.

Moreover, a device of either FIG. 1, FIG. 2 or FIG. 3 type is admirably suited for the continuous administration of the antibiotic oxytetracycline to beef cattle from the rumen. This because such devices can easily be fabricated of a size, weight and shape as to be retained in the rumen of polygastric animals to release drug or similar agent thereto at a carefully controlled rate. Other variations on the basic theme would be readily apparent to the skilled artisan. Although particular configurations may be designed for specific body uses, e.g., for use in the stomach or rumen, uterus, vagina, bladder, etc., each of these configurations is applicable to use in other environments. For another example, an ocular insert can similarly easily be fabricated of a size and shape adapted for insertion in the eye, e.g., the cul-de-sac of the conjunctiva between the sclera of the eyeball and the lower lid, to be held in place against the eyeball by the pressure of the lid. Compare in this respect U.S. Pat. Nos. 3,416,530 and 3,618,604.

The membrane 36 of FIGS. 2 and 3 and that portion of the wall members defining the canister 12 of FIG. 1 which exhibits controlled permeability to external fluids can be formed from a wide variety of materials permeable or semi-permeable to solvent but not to solute, i.e., those suitable for the construction of an osmotic cell. For best results, the membrane should be substantially impermeable to passage of the osmotically effective solute so as to prevent loss thereof. Typical membranes are isotropic membranes such as unplasticized cellulose acetate, plasticized cellulose acetate, reinforced cellulose acetate, cellulose di- and triacetate, ethyl cellulose; anisotropic reverse osmosis membranes which typically are made of cellulose acetate; silicone rubbers, polyurethanes, natural rubber, and hydrolyzed ethylene/vinyl acetate copolymers. Isotropic membranes have less water permeability than do the anisotropic membranes. Also, with both types of membranes, increasing the acetate content of the cellulose acetate polymer decreases the water permeability. Since, as previously described, the surface area of the membrane is relatively limited in a device of FIG. 2 type, it will be preferred to use semi-permeable membranes allowing relatively rapid water transmission in this general category of dispensers. Thus, in such embodiments the anisotropic membranes are the preferred. A cellulose acetate membrane suitable for this limited surface area application is Eastman Chemical Products Type RO 97, which is rated to be permeable to 1.5 to 2 cc/cm$^2$/day at atmospheric pressure, against a saturated solution of $K_2SO_4$ at 39° C. A specific example of the design of FIG. 2 constructed with polymethylmethacrylate dispensing head and having an inner diameter of 1.9 cm is capable of delivering 4 to 6 cc of active agent, advantageously a drug, per day. In one specific embodiment of a dispenser of FIG. 3 type, the membrane used was an isotropic cellulose acetate membrane, with no plasticizer, having an acetate substitution of 2.4, being 3 mils thick, and passing water at the rate of 70 mg/cm$^2$ per day against a saturated magnesium sulfate solution at 39° C. The membranes too are insoluble, and chemically compatible with the salt solution and any excess solute therein. For drug depot applications as heretofore described, the membranes are also biologically inert, non-irritating to body tissues and non-allergenic. For devices designed to deliver active agents relatively rapidly for a limited period, membranes of controlled high fluid permeability are indicated; membranes of lower fluid permeability are used to provide slower and more prolonged delivery.

The impermeable bag 14 of the osmotic dispensers of the figures of the drawing containing the active agent composition should be substantially impermeable both to fluid, and the other elements of the environment on which a device of such type is intended to be placed, the osmotically effective solute, and components of the active agent composition. Typical materials for use as the impermeable bag include polyethylene polyethylene terephthalate (Mylar), plasticized polyvinyl chloride, metal-foil polyethylene laminates, neoprene rubber, natural gum rubber, and Pliofilm (rubber hydrochloride). These materials are additionally flexible, insoluble and chemically compatible with the active agent therein, and, in the instance of providing a drug or like depot within the body of a living organism, are biologically inert, non-irritating to body tissues and non-allergenic.

The impermeable plastic canister 12 of FIGS. 2 and 3 and impermeable portions of the canister 12 of FIG. 1 too are insoluble and can be formed of polystyrene, polyethylene, polypropylene, polyvinyl chloride, reinforced epoxy resin, polymethylmethacrylate, etc., sheet metal (e.g., aluminum, copper, steel, etc.), galvanized pipe, or styrene/acrylonitrile copolymer. It is of course intended that such casing or shell act as a barrier to the transport of fluid, except at the areas of perforation. Again, for drug depot applications the same are advantageously biologically inert, non-irritating to body tissues and non-allergenic. The dispensing head 20 and the retaining ring 22 can be formed of materials identical to those used for fabricating the canisters 12 with polycarbonate being additionally well suited for the ring 22. Especially preferred of the above are the impermeable or refractory plastics.

Many other materials including those which are biologically acceptable are suitable for fabrication of the several component parts of the device of this invention. While the said several component parts of the device of the invention have previously been described as being insoluble under the conditions and in the environment of intended use, it is also within the scope of the invention that such materials be insoluble only during the period of said intended use; thereafter dissolving away in the environment of the device. Thus, a dispenser is here contemplated which is unaffected by its environment, solubility-wise, at the situs of use, or which is only slightly soluble during the period of intended use, such that once its active agent content has been discharged it will then dissolve or erode away leaving no objectionable residue or empty container at the said situs of use.

It is further within the scope of the invention to optionally provide the subject dispenser with a self-contained fluid supply or separate fluid compartment, as in the first mentioned Rose and Nelson publication, supra.

The relative thicknesses of the various membranes comprising the dispensers of the invention, as well as the relative thickness of the various canisters can vary widely and are not limitations on the invention. Typically, however, each canister has a wall thickness of 0.5 to 50 mils, preferably of 5 to 50 mils, and the fluid permeable membranes have a wall thickness of 1 to 10 mils.

Figure 4:
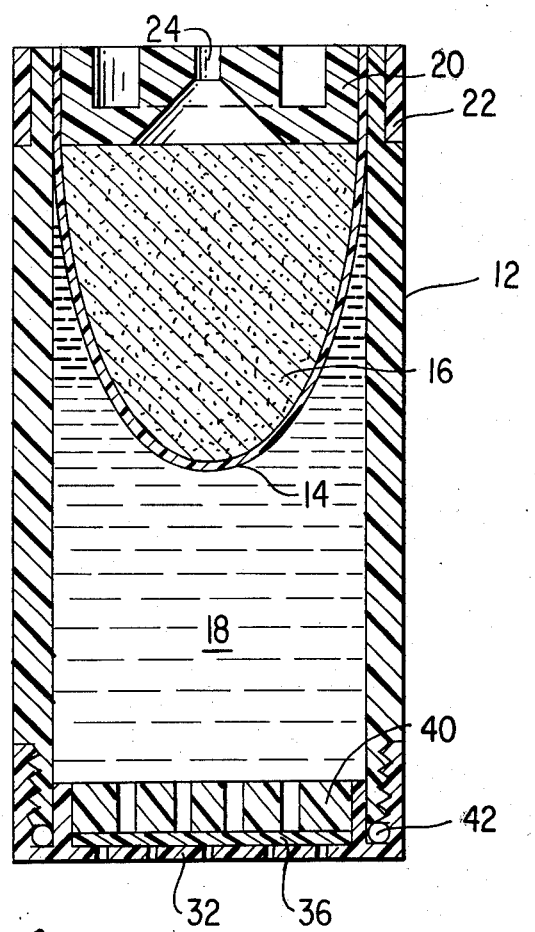
FIG. 4 is a cross-sectional view of still another osmotic dispenser of this invention.
Figure 5:
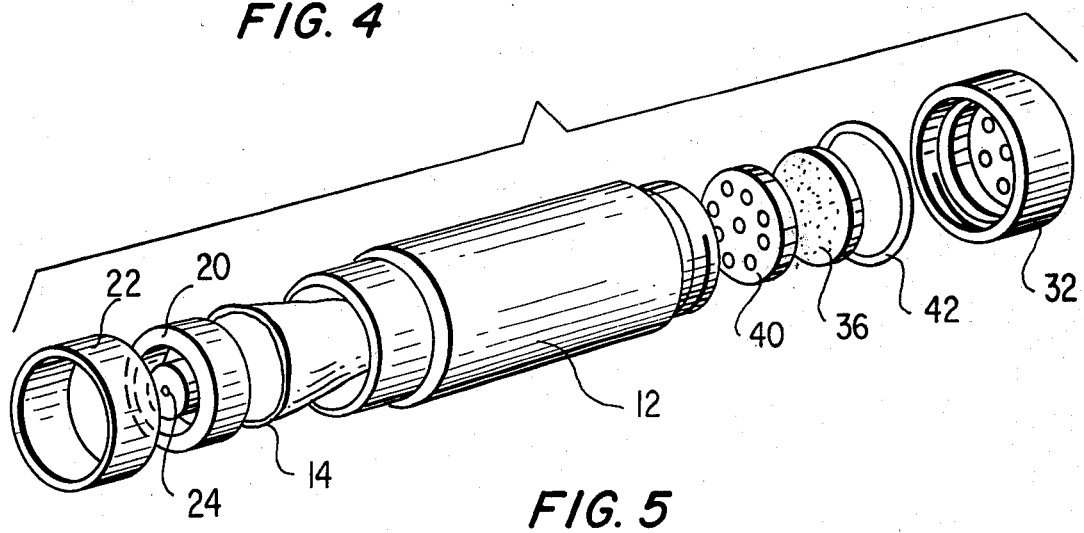
FIG. 5 is an exploded view of the dispenser of FIG. 4.

One specific embodiment of a dispenser fabricated in accordance with the invention, and as illustrated in FIGS. 4 and 5, fitted with a 3 mils thick semi-permeable membrane 36 and a 2 mils thick flexible active agent bag 14, and having the following dimensions and specifications:

| | |
|---|---|
| Outer diameter of dispenser | 1.125 inch |
| Wall thickness of canister 12 | .125 inch |
| Inner diameter of dispenser | .875 inch |
| Overall length | 2.5 inch |
| External volume | 2.45 inch$^3$ |
| Internal volume | 1.24 inch$^3$ |
| Overall dispenser density | 1.5 |
| Available membrane area | .44 inch$^2$ |
| Active agent volume | .94 inch$^3$ |
| Active agent density | 1.2 |
| Active agent: | Approximately 60 percent tetracycline hydrochloride dispersed in 40 percent polyethylene glycol medium; |
| Osmotic solution: | Saturated aqueous solution of $K_2SO_4$ containing sufficient excess solute in solid form to maintain solution saturated over a period of at least 3 days; |
| Water permeable membrane: | Cellulose diacetate, with a degree of acetyl substitution of 2.4; |
| Canister 12: | Soft polyethylene; |
| Threaded end cap 32: | Soft polyethylene; |
| Delivery cap 20: | Soft polyethylene; |
| Active agent bag 14: | Polyethylene; |
| Chamfered ring 22: | Polycarbonate; |
| Membrane support 40: | Polystyrene; |
| Diameter of delivery port 24: | .0625 inch; |
| Diameter of orifices in cap 32: | .0625 inch; |
| Diameter of orifices in support 40: | .1250 inch; | is capable of delivering 5 gm of the active drug per day, over a period of 3 days, when administered to the rumen of a five-hundred pound calf, whereat it is retained, via the gastrointestinal tract. It will be appreciated that the design of the FIG. 4 and FIG. 5 device is quite similar to that of FIG. 2, with the most salient distinctions therebetween residing, in the FIG. 4 and 5 device, in the perforated end cap construction 32 which is threaded onto the canister 12 and fitted with a rubber O-ring 42 to prevent leakage at the point of the thread fit. The cap 32 houses the membrane 36 and the membrane support 40. Of course, the greater the free space or total open surface area of the plurality of ducts bored into the end cap 32, the greater the amount of the membrane 36 which is exposed to the aqueous or other fluid environment. Likewise, the greater the open surface area of the plurality of ducts bored into the membrane support 40, the more readily the fluid diffuses into the compartment 24. As in the designs of FIGS. 2 and 3, it is again optional that a separator of porous paper, fabric or the like can be placed between either or both of the membrane support 40 and end cap 32 and the semi-permeable membrane 36. Same, as heretofore mentioned, prevents the membrane from being punctured or drawn into too tight a contact with its housing, thereby additionally assuring that the entire membrane is exposed to the aqueous environment.

In still another embodiment in accordance with this invention, hereinafter designated the "mini-pump" embodiment and as illustrated in the schematic drawing of FIG. 6, a modular osmotic active agent dispenser is constructed which is conceptually similar to the devices illustrated in the FIGS. 1 – 3. For the fabrication of the drug bag for the mini-pump, corresponding to the bag 14 of FIG. 1, there are first selected the raw materials consisting of (1) thin walled polyethylene tubing of a size according to the drug volume required, (2) two identical polyethylene 20 delivery and fill tubes (each having, e.g., 0.043 inch outer diameter and 0.015 inch inner diameter) and (3) a, for example, 0.010 inch needle or wire cleaner. Note the step I of FIG. 6. Next, as illustrated in the step II of FIG. 6, the wire is placed within the polyethylene 20 tubes and the resultant construction is arranged within the prospective drug bag, as depicted. The delivery and fill tubes are then heat sealed on Vertrod to either end of the larger drug bag polyethylene tubing and the wire is removed. In step III, via the fill tube conduit, the drug bag is filled with drug formulation, either in solution form or otherwise. An added overflow tube catches and retains drug formulation displaced as the bottom end of the device is sealed. This overflow tube is then removed and the delivery tube is sealed at its end. The final preparation of the drug bag is illustrated in step IV wherein the fill tube is removed by severing, the various seals are trimmed to minimize their size, and the delivery tube is roughened with emery paper. At this point in the operation the drug bag containing the drug formulation is conveniently pressure tested by mere squeezing.

Figure 6:
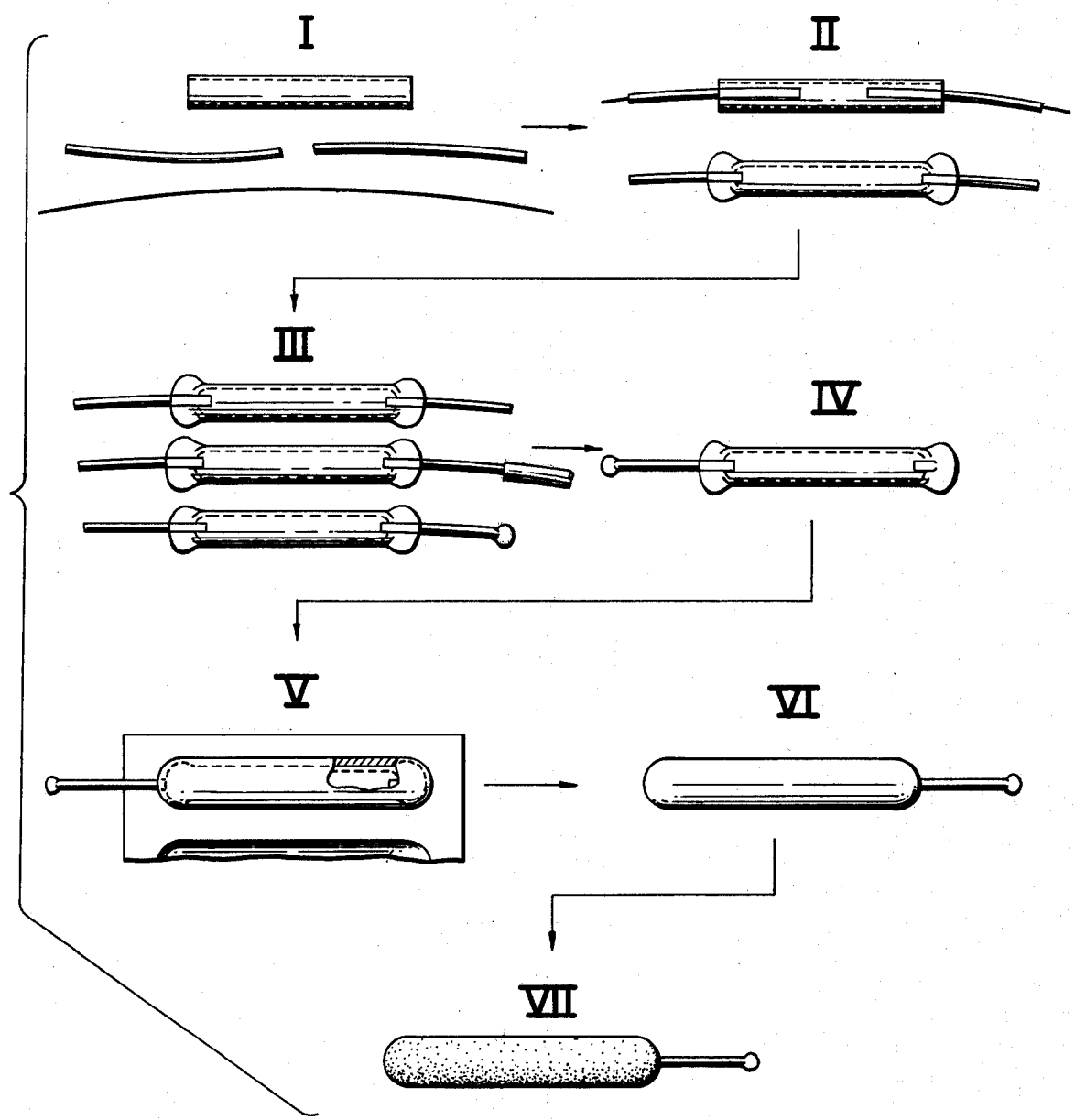
FIG. 6 is a schematic view of the construction and fabrication of still another osmotic dispenser of this invention, designated as the "mini-pump" embodiment.

The ultimate mini-pump construction is completed by following the procedures outlined in the steps V–VII of FIG. 6. First is a salt encapsulation, namely, a mold (not shown) is filled with a gelatin-salt matrix (by "salt" there is intended any of those osmotically effective solutes hereinafter described); the previously fabricated drug bag is then placed in the said mold and some is compressed by any convenient means (not shown), for example, a typical C-clamp. Next, the mold, bag and gelatine-salt matrix are frozen. Half of the mold is then removed and the half containing the pump fabrication is dried overnight in an oven. See step V for the appearance of the mini-pump subsequent to the encapsulation technique. Optionally, see step VI, the salt encapsulated drug bag can be coated with a thin layer of gelatin, by simply dipping same in a gelatin solution and permitting the coating to dry to hardness, to form a smooth surface more susceptible to the membrane coating operation of step VII. In step VII the construction of the mini-pump is completed by coating either the step V or step VI assembly with a layer of membrane material of the type previously described. For example, such assemblies can conveniently be coated by more dipping in an, e.g., cellulose acetate solution, permitting one hour to lapse between successive dips, and thence drying the thus membrane-coated construction for about 48 hours. The membrane coat is sufficiently rigid in and of itself such that as water permeates from an external aqueous environment through said permeable membrane coat and migrates by osmosis into the salt, thus forming an osmotically effective solution therewith which initiates the phenomenon of osmosis due to the tendency towards osmotic equilibrium with the said environment, the said membrane coat is able to withstand this increase in volume within the mini-pump and concomitant mechanical deflating force generated on the flexible drug bag, which force in turn ejects the active agent out of the dispenser at an osmotically controlled rate over a prolonged period of time.

The device of FIG. 6 is used exactly as the previously described dispensers, with the advantages of its smaller size being manifest (the illustrations of FIG. 6, for point of reference, are about twice actual size). For example, the distal end of the delivery tube an conveniently be cut off with a scalpel; placed, implanted or administered to a delivery environment; and the spent pump evidences complete discharge or delivery of its content. The various materials comprising the said mini-pump, moreover, substantially correspond to those materials comprising equivalent and corresponding components of those osmotic dispensers heretofore described and illustrated.

Figure 7:
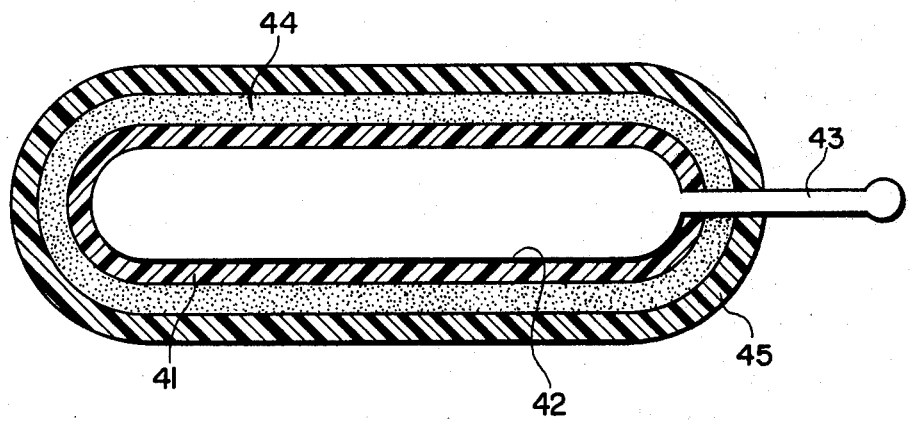
FIG. 7 is a cross-sectional view of another "mini-pump" osmotic dispenser of this invention.

The novel and useful osmotic agent dispensing device of FIG. 6 as manufactured according to the mode and manner of the invention, and as disclosed above, is not to be construed as limiting as these and other embodiments can also be fabricated in accordance with the spirit of the invention. For example, the device of FIG. 6 is manufactured, as shown in FIG. 7, of a wall 41 comprised of a flexible, collapsible material essentially impermeable to a fluid and substantially impermeable to an agent. The wall surrounds a chamber or bag defined by the wall's inner surface 42 as a means for containing the agent.

The agent can be added at the time the device is first made or the device can be stored and charged with the agent at a future time. Suitable materials for forming the wall are the impermeable materials set forth above and these include polyethylene, polypropylene, polyethylene terephthalate, plasticized polyvinyl chloride, polypropylene laminated with metal foils such as thin tin, polypropylene laminated with metal foils such as thin tin, aluminum foil, cross-linked polyester, commercially available copolymers, and the like. The device is provided with a means 43 for releasing the agent from the chamber to the exterior of the osmotic dispensing device, and this releasing means can be a passageway that communicates with the chamber and the exterior environment, a capillary, a porous fiber, a sintered plug and the like. Distant from the means for releasing the agents is optionally located a filling port, not shown in FIG. 7, that communicates with the chamber that is integrally formed or suitably joined to the osmotic dispensing device. The filling port can be a silicon plug, an impermeable cross-linked rubber diaphragm pierceable by a filling needle, a tube that can be closed after the chamber is filled by heating and squeezing the tube, a valve, and the like. The impermeable wall bears on its outer surface a coating 44 comprised of at least one compound that can exhibit an osmotic pressure gradient against a fluid when the device is subsequently placed in the environment of use. The osmotically effective compound is applied to the wall by standard methods such as dipping, spraying, depositing, laminating, filming and the like to give the corresponding coat, film, laminate and the like; and, which methods and results are deemed for the purpose of this invention as functional equivalents. Representative of osmotically effective compounds suitable for this purpose, are inorganic and organic compounds such as magnesium sulphate, magnesium chloride, sodium chloride, lithium chloride sodium carbonate, sodium succinate, mixtures thereof, and other osmotic attractants as described in this disclosure. The compounds can be applied in pure form, that is, by mixing the compound with a suitable solvent followed by dipping or brushing the solution onto the walls and then evaporating the solvent. The compound can also be applied by mixing it with a binder such as ethylcellulose, gelatin, ethylmethylcellulose, hydroxypropul methyl cellulose, sodium cellulose sulfate, polyvinylalcohol, polyethylene glycol, Irish moss, casein and the like, mixed with the binder alone, or with a solvent which is applied to the wall by standard techniques. The amount of binder mixed with the compound is an amount sufficient to bind the compound to the wall and it is usually, when used, about 0.001% to 20% or higher, for 1 to 1000 grams of compound. When a solvent is used any conventional inorganic or organic solvent that does not adversely affect the parts of the device and can be suitably removed by evaporation, drying, and the like can be used as a manufacturing means.

Distant from the inner impermeable wall, that is, the outer wall of the osmotic device, and in proximate contact with the osmotically effective compounds is a wall 45 comprised in at least a part of a semi-permeable membrane that lets an external fluid permeate therethrough while being substantially impermeable to the osmotic attractants. These membranes are applied by conventional techniques and they include cellulose acetate, reinforced cellulose acetate, polyurethanes, and the semi-permeable membranes as disclosed in this specification. This device offers an improved advantage that it can be filled and stored without any adverse effects on the agent or its release from the device since the device commences operation when placed in the environment of use.

Any of the drugs used to treat the animals, including humans and avians, both topical, local and systemic, can be compartmentalized as the active agent in any of the osmotic dispensers of this invention. "Drug" is used herein in its broadest sense as including any composition or substance that will produce a pharmacological or physiological response.

Suitable drugs for use in therapy with the dispenser of the invention include without limitation:

1. Protein drugs such as insulin;
2. Desensitizing agents such as ragweed pollen antigens, hay fever pollen antigens, dust antigen and milk antigen;
3. Vaccines such as small pox, yellow fever, distemper, hog cholera, fowl pox, antivenom, scarlet fever, diphtheria toxoid, tetanus toxoid, pigeon pox, whopping cough, influenzae, rabies, mumps, measles, poliomyelitis, Newcastle disease, etc.;
4. Anti-infectives, such as antibiotics, including penicillin, tetracycline, chlortetracycline, bacitracin, nystatin, streptomycin, neomycin, polymyxin, gramicidin, oxytetracycline, chloramphenicol, and erythromycin; sulfonamides, including sulfacetamide, sulfamethizole, sulfamethazine, sulfadiazine, sulfamerazine, and sulfisoxazole; anti-virals including idoxuridine; and other anti-infectives including nitrofurazone and sodium propionate;
5. Anti-allergenics such as antazoline, methapyrilene, chlorpheniramine, pyrilamine and prophenpyridamine;
6. Anti-inflammatories such as hydrocortisone; cortisone, hydrocortisone acetate, dexamethasone, dexamethasone 21-phosphate, fluocinolone, triamcinolone, medrysone, prednisolone, prednisolone 21-phosphate, and prednisolone acetate;

7. Decongestants such as phenylephrine, naphazoline, and tetrahydrozoline;

8. Miotics and anticholinesterases such as pilocarpine, eserine salicylate, carbachol, di-isopropyl fluorophosphate, phospholine iodide, and demecarium bromide;

9. Mydriatics such as atropine sulfate, cyclopentolate, homatropine, scopolamine, tropicamide, eucatropine, and hydroxy-amphetamine;

10. Sympathomimetics such as epinephrine;

11. Sedatives and hypnotics such as pentobarbital sodium, phenobarbital, secobarbital sodium, codeine, ($\alpha$-bromo-isovaleryl) urea, carbromal;

12. Psychic energizers such as 3-(2-aminopropyl) indole acetate and 3-(2-aminobutyl) indole acetate;

13. Tranquilizers such as reserpine, chlorpromazine, and thiopropazate;

14. Androgenic steroids such as methyltestosterone and fluoxymesterone;

15. Estrogens such as estrone, 17 $\beta$-estradiol, ethinyl estradiol, and diethyl stilbesterol;

16. Progestational agents such as progesterone, megestrol, melengestrol, chlormadinone, ethisterone, norethynodrel, 19-nor-progesterone, norethindrone, medroxyprogesterone and 17 $\alpha$-hydroxy-progesterone;

17. Humoral agents such as the prostaglandins, for example, $PGE_1$, $PGE_2$, and $PGF_2$;

18. Antipyretics such as aspirin, sodium salicylate, and salicylamide;

19. Antispasmodics such as atropine, methantheline, papaverine, and methscopolamine bromide;

20. Anti-malarials such as the 4-aminoquinolines, 8-aminoquinolines, chloroquine, and pyrimethamine;

21. Antihistamines such as diphenhydramine, dimenhydrinate, tripelennamine, perphenazine, and carphenazine;

22. Cardioactive agents such as hydrochlorothiazide, flumethiazide, chlorothiazide, and trolnitrate;

23. Nutritional agents such as vitamins, essential amino acids and essential fats;

24. Anti-Parkinsonism agents such as L-dopa, (L-3,4-dihydroxyphenylalanine);

25. Investigative antihypotensive agents such as dopamine, 4-(2-aminoethyl) pyrocatechol.

Other drugs having the same or different physiological activity as those recited above can be employed in osmotic dispensers within the scope of the present invention. Suitable mixtures of drugs can, of course, be dispensed with equal facility as with single component systems.

Drugs can be in various forms, such as uncharged molecules, components of molecular complexes, or non-irritating pharmacologically acceptable salts such as hydrochloride, hydrobromide, sulphate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the osmotic dispenser varies widely depending on the particular drug, the desired therapeutic effect, and the time span for which it takes the drug to be released. Since a variety of dispensers in a variety of sizes and shapes are intended to provide complete dosage regimes for therapy for a variety of maladies, there is no critical upper limit on the amount of drug incorporated in the dispenser. The lower limit too will depend on the activity of the drug and the time span of its release from the dispenser. Thus it is not practical to define a range for the therapeutically effective amount of drug to be released by the dispenser.

The motive force of the dispenser of this invention depends on the osmotic pressure generated by the solution 18 of the osmotically effective solute confined within the canister 12, which solution exhibits an osmotic pressure gradient against a given fluid. Said solution is most preferably a saturated aqueous salt solution. To maintain the solution saturated and therefore to achieve a constant osmotic pressure throughout operation of the dispenser, the canister containing the solution also contains excess solute in solid form. Various osmotically effective solutes can be used. These include magnesium sulphate, magnesium chloride, sodium chloride, potassium sulphate, sodium carbonate, sodium sulphite, sodium sulphate, sodium bicarbonate, potassium acid phthalate, calcium bicarbonate, potassium acid phosphate, raffinose, tartaric acid, succinic acid, calcium succinate, calcium lactate, and magnesium succinate. The excess solid solute can be in the form of dispersed particles or preferably in the form of a pellet. The solution can initially be a solution of the same or of an osmotically effective solute different than the solid excess solute.

The osmotic dispenser can be fabricated in any convenient shape for either physical insertion or implantation in the body, or for administration via the gastrointestinal tract, or for introduction into any desired fluid environment. Dimensions of the device can thus vary widely and are not of controlling importance. The lower limit of the size of the device is governed by the amount of the particular active agent to be supplied to the fluid environment to elicit the desired response, as well as by the form the dosage unit takes, for example, in cases of specific body uses, implantate, bolus, IUD, IVD, vaginal ring, ocular insert, bladder insert, uterine capsule for fertility suppression, artificial gland, pessary, prosthesis, suppository, and the like. Likewise with respect to the upper limit on the size of the device. In one specific embodiment, the dispenser can be of such size as to deliver 1 to 2 cc of drug formulation per day and to deliver a total of 5 to 10 cc of drug formulation over a 5 to 10 day period. With alternate choices of slower permeation membranes, the pump can deliver drug more slowly up to and in excess of one year. It is preferred that the construction of the canister and of the active agent release means be such that the osmotic driving pressure developed is at least ten times greater than the back pressure generated by the active agent formulation.

Thus, the invention provides, in an osmotic dispenser, a reliable means for releasing effective concentrations of active agent contained therein to the body of a living organism, or to any other fluid environment, at an osmotically controlled rate and over a prolonged period of time. In addition, prime advantages of the dispenser of the invention are that it is simple in construction and exhibits all of the practical advantages of the long-term continuous administration of various active agents both to humans, animals, and into other environments, and that the active agent contained therein will not exhibit the tendency to be leached therefrom.

While the invention has been described and illustrated with reference to certain preferred embodiments thereof, those skilled in the art will appreciate that various modifications, changes, omissions, and substitutions can be made without departing from the spirit of the invention. It is intended, therefore, that the invention be limited only by the scope of the following claims.

What is claimed is:

1. An osmotic active agent dispenser comprising a bag formed of a flexible, relatively impervious material as a means for containing an active agent and provided with a means for releasing the active agent to the exterior of the device, the bag encapsulated with a film comprised of an osmotically effective solute which solute when in solution exhibits an osmotic pressure gradient against an external fluid, the film surrounded by a wall comprised of a shape retaining material having in at least a part controlled permeability to the exterior fluid, and wherein in operation when the bag is charged with at least one active agent, the agent is dispensed from the device by fluid permeating from the external environment through the permeable wall producing a solution of the solute in a tendency towards osmotic equilibrium with said environment, same increasing the volume between the wall and the bag thereby generating mechanical deflating forces on the bag, which in turn ejects the active agent out of the dispenser at an osmotically controlled rate over a prolonged period of time.

2. An osmotic active agent dispenser as defined by claim 1 wherein the device is provided with a filling port.

3. An osmotic active agent dispenser as defined by claim 1 wherein the film of the osmotically effective solute contains a binder and the film is in contact with the bag.

4. An osmotic active agent dispenser as defined by claim 1 wherein the device is adapted for dispensing an active agent in the stomach.

5. An osmotic active agent dispenser as defined by claim 1 wherein the device is adapted for dispensing an active agent in the vagina.

6. An osmotic active agent dispenser as defined by claim 1 wherein the device is adapted for dispensing an active agent in the uterus.

7. An osmotic active agent dispenser as defined by claim 1 wherein the device is adapted for dispensing an active agent to the eye.

8. An osmotic active agent dispenser as defined by claim 1 wherein the device is adapted for dispensing an active agent in the bladder.

9. An ocular osmotic dispenser for dispensing an ophthalmic agent comprising,
   a. an inner wall formed of a flexible material, relatively impervious to tear fluid, osmotic solutes and an ophthalmic agent, the wall surrounding and forming,
   b. a compartment defined by the wall's inner surface which compartment contains an ophthalmic agent and is provided with a means for dispensing the agent to the exterior of the device,
   c. a layer of an osmotically effective solute deposited on the wall's outer surface, said solute exhibiting an osmotic pressure gradient against tear fluid when the dispenser is placed in the environment of use,
   d. an outer wall intimately surrounding the layer of the solute, said wall comprised of a material having shape retaining properties, permeable to a tear fluid and substantially impermeable to the solute, and,
   e. wherein in operation in the environment of use the ophthalmic agent is dispensed from the device by tear fluid permeating from the exterior through the permeable outer wall producing a continuous solution of the solute in a tendency towards osmotic equilibrium with the environment thereby continually increasing the volume between the outer wall and the compartment generating a mechanical force causing the compartment to continuously collapse and dispense the ophthalmic agent from the device at a controlled rate over a prolonged period of time.

10. An ocular osmotic dispenser for dispensing an ophthalmic agent as defined by claim 7 wherein the agent is pilocarpine.

* * * * *

UNITED STATES PATENT AND TRADEMARK OFFICE
CERTIFICATE OF CORRECTION

PATENT NO. : 3,995,631
DATED : December 7, 1976
INVENTOR(S) : Takeru Higuchi and Harold Leeper and Felix Theeuwes It is certified that error appears in the above-identified patent and that said Letters Patent are hereby corrected as shown below:

In column 4, at line 27, please delete "mini-pump" and substitute therefor --mini-osmotic pump--.

At column 10, lines 6, 9 and 35, please delete references to "mini-pump" and substitute therefor --mini-osmotic pump--.

At column 11, lines 2 and 15, please delete the references to "mini-pump" and substitute therefor --mini-osmotic pump--.

Signed and Sealed this

Fourteenth Day of October 1980

[SEAL]

Attest:

SIDNEY A. DIAMOND

Attesting Officer

Commissioner of Patents and Trademarks